United States Patent [19]

Martel et al.

[11] 4,357,335
[45] Nov. 2, 1982

[54] SUBSTITUTED PYRIDINE METHYL ESTERS OF DIMETHYL CYCLOPROPANE CARBOXYLIC ACIDS AND THEIR USE AS INSECTICIDES

[75] Inventors: Jacques Martel, Bondy; Jean Tessier, Vincennes; André Teche, Paris; Jean-Pierre Demoute, Montreuil-sous-Bois, all of France

[73] Assignee: Roussel Uclaf, Paris, France

[21] Appl. No.: 280,547

[22] Filed: Jul. 6, 1981

[30] Foreign Application Priority Data

Jul. 4, 1980 [FR] France ................. 80 14967

[51] Int. Cl.³ .................... A61K 31/44; C07D 213/55
[52] U.S. Cl. .................................... 424/263; 546/270; 546/283; 546/284; 546/300; 546/301; 546/302
[58] Field of Search ............... 546/300, 301, 302, 270, 546/284, 283; 424/263

[56] References Cited

U.S. PATENT DOCUMENTS

| | | | |
|---|---|---|---|
| 4,221,799 | 9/1980 | Van Heertum et al. | 546/300 |
| 4,223,033 | 9/1980 | Henrick | 546/300 |
| 4,228,172 | 10/1980 | Malhotra et al. | 546/300 |
| 4,238,614 | 12/1980 | Henrick | 546/301 |
| 4,256,893 | 3/1981 | Malhotra et al. | 546/301 |
| 4,264,606 | 4/1981 | Ozawa et al. | 546/300 |
| 4,281,133 | 7/1981 | Malhotra et al. | 546/300 |
| 4,285,954 | 8/1981 | Brown et al. | 546/301 |
| 4,315,012 | 2/1982 | Martel et al. | 546/300 |

*Primary Examiner*—Jane T. Fan
*Attorney, Agent, or Firm*—Hammond & Littell, Weissenberger and Muserlian

[57] ABSTRACT

Novel esters in all possible isomeric forms and mixtures thereof of the formula

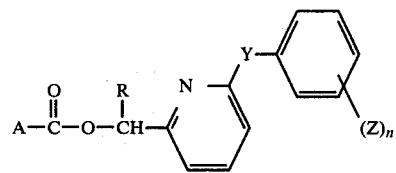

wherein A is selected from the group consisting of

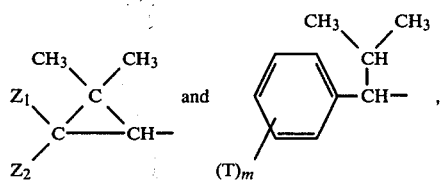

R is selected from the group consisting of hydrogen, —CN and —C≡CH, Y is selected from the group consisting of oxygen and sulfur, Z is selected from the group consisting of alkyl and alkoxy of 1 to 4 carbon atoms, alkylthio and alkylsulfonyl of 1 to 4 carbon atoms, cycloalkyl of 3 to 4 carbon atoms, 3,4-methylenedioxy, chlorine, fluorine and bromine, n is an integer of 0, 1 or 2, $Z_1$ and $Z_2$ may both be methyl or $Z_1$ is hydrogen and $Z_2$ is

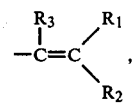

$R_3$ is selected from the group consisting of hydrogen and halogen, $R_1$ and $R_2$ are individually alkyl of 1 to 8 carbon atoms or taken together with the carbon they are attached to form cycloalkyl of 3 to 6 carbon atoms or

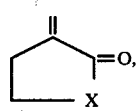

X is selected from the group consisting of oxygen and sulfur, T is at least one member of the group consisting of halogen, alkyl of 1 to 8 carbon atoms, alkoxy of 1 to 8 carbon atoms optionally substituted with at least one halogen and —CF₃ and m is an integer from 0, 1 or 2 having insecticidal activity as well as nematocidal and acaricidal activity.

28 Claims, No Drawings

SUBSTITUTED PYRIDINE METHYL ESTERS OF DIMETHYL CYCLOPROPANE CARBOXYLIC ACIDS AND THEIR USE AS INSECTICIDES

STATE OF THE ART

French Pat. No. 2,383,927 describes pyridyl methyl esters of cyclopropane-carboxylic acid having a dihalovinyl group in the 3-position of the cyclopropane ring.

OBJECTS OF THE INVENTION

It is an object of the invention to provide the novel esters of formula I and a process for their preparation.

It is another object of the invention to provide novel compositions as well as a novel method of combatting pests including insects, nematodes and acariens of vegetables and warm-blooded animals.

These and other objects and advantages of the invention will become obvious from the following detailed description.

THE INVENTION

The novel compounds of the invention are esters in all possible isomeric forms and mixtures thereof of the formula

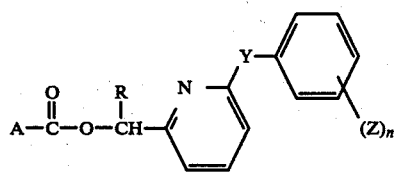
I wherein A is selected from the group consisting of

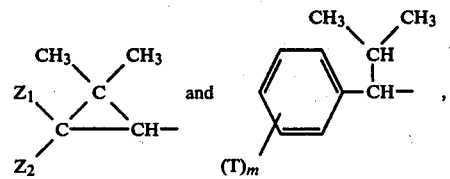

R is selected from the group consisting of hydrogen, $-CN$ and $-C\equiv CH$, Y is selected from the group consisting of oxygen and sulfur, Z is selected from the group consisting of alkyl and alkoxy of 1 to 4 carbon atoms, alkylthio and alkylsulfonyl of 1 to 4 carbon atoms, cycloalkyl of 3 to 4 carbon atoms, 3,4-methylenedioxy, chlorine, fluorine and bromine, n is an integer of 0, 1 or 2, $Z_1$ and $Z_2$ may both be methyl or $Z_1$ is hydrogen and $Z_2$ is

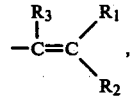

$R_3$ is selected from the group consisting of hydrogen and halogen, $R_1$ and $R_2$ are individually alkyl of 1 to 8 carbon atoms or taken together with the carbon they are attached to form cycloalkyl of 3 to 6 carbon atoms or

X is selected from the group consisting of oxygen and sulfur, T is at least one member of the group consisting of halogen, alkyl of 1 to 8 carbon atoms, alkoxy of 1 to 8 carbon atoms optionally substituted with at least one halogen and $-CF_3$ and m is an integer from 0, 1 or 2.

Examples of $R_3$ are hydrogen, fluorine, chlorine and bromine. Examples of $R_1$ and $R_2$ are alkyl such as methyl, ethyl or propyl and cycloalkyl such as cyclopropyl, cyclobutyl, cyclopentyl or cyclohexyl.

Examples of T are halogens such as chlorine, alkyl such as methyl, ethyl or propyl, alkoxy optionally substituted with halogen such as methoxy, ethoxy, propoxy or $-OCHF_2$.

Examples of Z are alkyl such as methyl, ethyl, propyl, isopropyl, n-butyl, isobutyl or tert.-butyl, cycloalkyl of 3 to 4 carbon atoms such as cyclopropyl and cyclobutyl, alkoxy such as methoxy, ethoxy, propoxy, isopropoxy, butoxy, isobutoxy and tert.-butoxy and alkylthio and alkylsulfonyl such as methylthio, methylsulfonyl, ethylthio, ethylsulfonyl, propylthio, isopropylthio, butylthio, isobutylthio, tert.-butylthio, propylsulfonyl, isopropylsulfonyl, butylsulfonyl, isobutylsulfonyl and tert.-butylsulfonyl.

Among the preferred compound of the invention are those wherein Y is oxygen, those wherein n is 0, those wherein R is $-CN$ and those wherein A is

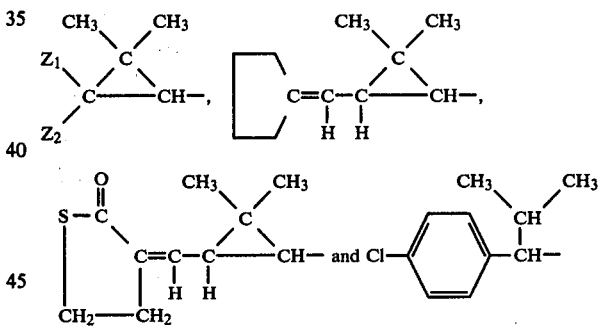

The novel process for the preparation of the compounds of formula I comprises reacting an acid of the formula

II or a functional derivative thereof wherein A has the above definition with an alcohol of the formula

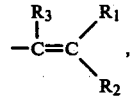
III wherein R, Y, Z and n have the above definitions to form the compound of formula I in a mixture of its isomers which may be separated, if desired, by physical methods into the individual isomers. The functional acid derivatives is preferably the acid anhydride or acid halide such as the acid chloride and the reaction with the alcohol of formula III is effected in the presence of dicyclohexylcarbodiimide or diisopropylcarbodiimide.

The novel pesticidal compositions of the invention are comprised of a pesticidally effective amount of at least one compound of formula I and an inert carrier. The compositions are useful to combat pests such as parasites of vegetables and of warm-blooded animals as well as parasites of premises and are particularly useful to combat insects, nematodes and parasitic acariens which attack warm-blooded animals and vegetables and may be used as additives to animal feeds.

The compositions of the invention are particularly useful to combat insects in the agricultural field, for example, to control aphides and larvae of lepidoptera and coleoptera and are usually used at a dose of 10 to 300 g of the compounds of formula I per hectare. The compositions are also useful to control insects in the premises, for example to combat flies, mosquitoes and beetles.

The pesticidal compositions of the invention are useful to combat vegetable parasitic acariens and nematodes as well as to combat animal parasitic acariens such as ticks, especially ticks of Boophilus species, Hyalomnia species, Amblyomnia species and Rhipicephalus species and to combat all sorts of scabies such as sarcoptic scabies, psoroptic scabies and chorioptic scabies.

The invention also includes compositions intended to combat parasites of warm-blooded animals parasites of premises and parasites of vegetables by the use of at least one compound of formula I.

For the compositions intended for domestic or agricultural use, the compositions may also contain one or more other pesticidal agents. The compositions may be in the form of powders, granules, suspensions, emulsions, solutions, aerosol solutions, combustible bands and baits or other preparations classically used for compounds of this type.

Besides the active ingredient, the compositions generally contain a vehicle and/or a nonionic surface active agent to ensure a uniform dispersion of the substances in the mixture. The vehicle used may be a liquid such as water, alcohol, hydrocarbons or other organic solvents or a mineral, animal or vegetable oil or a powder such as talc, clays, silicates or Kieselguhr or a combustible solid. The insecticidal compositions usually contain 0.005 to 10% by weight of the compounds of formula I.

The insecticidal compositions as well as the acaricidal and nematocidal compositions of the invention may also contain one or more other pesticides and are in the usual powder, granule, suspension, emulsion or solution form. For acaricide use, the compositions are preferably wettable powders for foliar spraying containing 1 to 80% of liquids for foliar spraying containing 1 to 500 g/l of the active ingredient. Also useful are powders for foliar powdering containing 0.5 to 3% by weight of the active ingredient. For nematocide use, the compositions are in the form of liquids for soils treatment containing 300 to 500 g/l of the active ingredient. For acaricide and nematocide use, the preferred dose of the active compounds is 1 to 100 g per hectare.

To increase the biological activity of the compositions of the invention, classical synergists may be incorporated therein such as 1-(2,5,8-trioxadodecyl)-2propyl-4,5-methylenedioxy-benzene (piperonyl butoxide) or N-(2-ethyl-heptyl)-bicyclo-[2,2-1]5-heptene-2,3-dicarboximide or piperonyl-bis-2-(2'-n-butoxy-ethoxy)-ethyl acetal (tropital).

When the compositions are to be used to combat warm-blooded animal parasitic acariens, the active compounds of formula I are very often incorporated into alimentary compositions in association with a nutritive mixture adapted to the animal to be fed. The nutritive mixture will vary depending upon the specific animal but usually contains cereals, sugars and grains, soybean press cake, peanuts and turnsole, meal of animal origin such as fish meal, synthetic amino acids, mineral salts, vitamins and antioxidants.

The compositions of the invention show an excellent general tolerance and are equally useful as medicaments for treating affections created by ticks and scabies. The compositions may be used in veterinary and human medicines. In human medicine, the compositions may be used to prevent or treat lice as well as combat scabies. The compositions may also be used as anthelmintics.

The said medicaments may be administered externally by vaporization, by painting or by bathing. For veterinary usage, the compositions may also be administered by painting the dorsal spine by the "pour on" method as well as being administered digestively or parenterally.

The compositions of the invention are also useful as biocides or to regulate growth.

The novel method of the invention for combatting parasites such as insects, nematodes and acariens comprises contacting the parasites with a pesticidally effective amount of at least one compound of formula I.

In the following examples there are described several preferred embodiments to illustrate the invention. However, it should be understood that the invention is not intended to be limited to the specific embodiments.

EXAMPLE 1

(RS)α-cyano-(6-phenoxy-2-pyridyl)-methyl (1R,trans) 2,2-dimethyl-3-(cyclopentylidenemethyl)-cyclopropane-1-carboxylate 0.4 ml of pyridine and 1.031 g of dicyclohexylcarbodiimide were added to a solution of 0.971 g of (1R,trans) 2,2-dimethyl-3-(cyclopentylidenemethyl)-cyclopropane-1-carboxylic acid in 15 ml of methylene chloride and then 1.13 g of (RS)α-hydroxy-6-phenoxy-2-pyridine-acetonitrile were added thereto. The mixture was stirred at 22° C. for 90 minutes and was then filtered. The filtrate was washed with water, dried and evaporated to dryness under reduced pressure. The 2.9 g of residue was chromatographed over silica gel and eluted with a 9-1 cyclohexane-ethyl acetate mixture yielded 718 mg of (RS)α-cyano-(6-phenoxy-2-pyridyl)-methyl (1R,trans) 2,2-dimethyl-3-(cyclopentylidenemethyl)-cyclopropane-1-carboxylate.

NMR Spectrum (deuterochloroform)

Peaks at 1.17–1.18–1.23–1.29 ppm (hydrogens of geminal methyls); at 1.45–1.54 ppm (1-hydrogen of cyclopropane); at 4.9–5 ppm (ethylenic hydrogen); at 6.3 ppm (hydrogen on carbon attached to CN); at 6.8–6.9 ppm (3- and 5-hydrogens of pyridine); at 7.6–7.9 ppm (4-hydrogen of pyridine); at 7 to 7.6 ppm (aromatic hydrogens).

EXAMPLE 2

(R,S)α-cyano-(6-phenoxy-2-pyridyl)-methyl tetramethyl-cyclopropane-carboxylate

Using the procedure of Example 1, tetramethylcyclopropane-carboxylic acid and (R,S)α-hydroxy-6-phenoxy-2-pyridine-acetonitrile were reacted to obtain (R,S)α-cyano-(6-phenoxy-2-pyridyl)-methyl tetramethyl-cyclopropane-carboxylate with a melting point of ≃68°–70° C.

NMR Spectrum (deuterochloroform)

Peaks at 1.23 and 1.27 ppm (hydrogens of methyls); at 6.27 ppm (hydrogen on carbon attached to —CN); at 6.8–6.92 ppm (3- and 5-hydrogens of pyridine); at 7.6–7.7–7.8 ppm (4-hydrogen of pyridine); at 7–7.4 ppm (other aromatic hydrogens).

EXAMPLE 3

R and S α-cyano-(6-phenoxy-2-pyridyl)-methyl (1R,cis, ΔE) 2,2-dimethyl-3-[(dihydro-2-oxo-3-(2H)-thienylidene)-methyl]-cyclopropane-carboxylate 0.8 ml of pyridine and 2.06 g of dicyclohexylcarbodiimide were added at 27° C. to a solution of 2.26 g of (1R,cis, ΔE) 2,2-dimethyl-3-[(dihydro-2-oxo-3-(2H)-thienylidene)-methyl]-cyclopropane-carboxylic acid in 30 ml of methylene chloride and then 2.26 g of (R,S)α-hydroxy-6-phenoxy-2-pyridine-acetonitrile were added thereto. The mixture was stirred for 2 hours and was then filtered and the filtrate was adjusted to a volume of 100 ml by addition of methylene chloride. The mixture was washed with 0.5 N hydrochloric acid and with water, was dried and evaporated to dryness under reduced pressure. The residue was chromatographed over silica gel and was eluted with a 7–3 cyclohexane-ethyl acetate mixture. The resulting 3.9 g of product was chromatographed over silica gel again and was eluted with a 97–3 benzene-ethyl acetate mixture to separate the R and S α-cyano-(6-phenoxy-2-pyridyl)-methyl (1R,cis ΔE) 2,2-dimethyl-3-[(dihydro-2-oxo-3-(2H)-thienylidene)-methyl]-cyclopropane-carboxylate.

NMR Spectrum (deuterochloroform)

R-isomer—peaks at 1.3 and 1.35 ppm (hydrogens of geminal methyls); at 1.7 and 2.08 ppm (1- and 3-hydrogens of cyclopropane); at 6.8 to 6.9 ppm (ethylene hydrogen attached to 3-position of cyclopropane); at 2.83 to 3.42 ppm (hydrogen of thienyl); at 6.3 ppm (hydrogen on carbon attached to —CN); at 7.6 to 7.8 ppm (4-hydrogen of pyridine).

S-isomer—peaks at 1.29 ppm (hydrogens of geminal methyls); at 6.7–6.8 ppm or 6.8 to 7 ppm (ethylenic hydrogen attached to 3-position of cyclopropane and 3- and 5-hydrogens of pyridine); at 2.83 to 3.5 ppm (hydrogen of thienyl); at 6.3 ppm (hydrogen on carbon attached to —CN); and 7.6 to 8 ppm (4-hydrogen of pyridine).

EXAMPLE 4

(R,S)α-cyano-(6-phenoxy-2-pyridyl)-methyl (1R,cis) 2,2-dimethyl-3-(cyclopentylidenemethyl)-cyclopropane-carboxylate A mixture of (1R,cis) 2,2-dimethyl-3-(cyclopentylidenemethyl)-cyclopropane-carboxylic acid and thionyl chloride in petroleum ether (b.p.=40° to 70° C.) was refluxed to obtain (1R,cis) 2,2-dimethyl-3-(cyclopentylidenemethyl)-cyclopropane-carboxylic acid chloride which was then reacted with R,S α-hydroxy-6-phenoxy-2-pyridine-acetonitrile in benzene in the presence of pyridine to obtain (R,S)α-cyano-(6-phenoxy-2-pyridyl)-methyl (1R,cis) 2,2-dimethyl-3-(cyclopentylidenemethyl)-cyclopropane-carboxylate.

EXAMPLE 5

(R,S)α-cyano-(6-phenoxy-2-pyridyl)-methyl (1R,trans, ΔE) 2,2-dimethyl-3-[(dihydro-2-oxo-3-(2H)-thienylidene)-methyl]-cyclopropane-carboxylate Using the procedure of Example 4, (1R, trans, ΔE) 2,2-dimethyl-3-[(dihydro-2-oxo-3-(2H)-thienylidene)-methyl]-cyclopropane-carboxylic acid was reacted to form its acid chloride which was then reacted with (R,S)α-hydroxy-6-phenoxy-2-pyridine-acetonitrile to form (RS)α-cyano-(6-phenoxy-2-pyridyl)-methyl (1R,trans ΔE) 2,2-dimethyl-3-[(dihydro-2-oxo-3-(2H)-thienylidene)-methyl]-cyclopropane-carboxylate.

EXAMPLE 6

(R,S)α-cyano-(6-phenoxy-2-pyridyl)-methyl (S) 4-chloro-α-isopropyl-benzeneacetate Using the procedure of Example 4, (S) 4-chloro-α-isopropyl-benzeneacetic acid was converted into its acid chloride which was then reacted with (R,S)α-hydroxy-6-phenoxy-2-pyridine-acetonitrile to obtain (R,S)α-cyano-(6-phenoxy-2-pyridyl)-methyl (S) 4-chloro-α-isopropyl-benzeneacetate.

EXAMPLE 7

An emulsifiable concentrate was prepared by homogeneously mixing 1.5 g of the product of Example 1, 20 g of Tween 80, 0.1 g of Topanol A and 78.4 g of xylene.

A soluble concentrate was prepared by homogeneously mixing 0.25 g of the product of Example 1, 1 g of piperonyl butoxide, 0.25 g of Tween 80, 0.1 g of Topanol A and 98.4 g of water.

Another emulsifiable concentrate was prepared by initimately mixing 0.015 g of the product of Example 1, 0.5 g of piperonyl butoxide, 0.1 g of Topanol A, 3.5 g of Tween 80 and 95.885 g of xylene.

A fumigant composition was prepared containing 0.25 g of the product of Example 1, 25 g of tabu powder, 40 g of powdered cedar needles, 33.75 g of powdered pine sawdust, 0.5 g of brilliant vert and 0.5 g of p-nitrophenol.

INSECTICIDAL STUDY

The insecticidal activity of the compound of Example 1 was determined on 4 day old female houseflies by topically applying 1 μl of an acetone solution of the test compound of the dorsal thorax of the insects with the aid of an Arnold micro manipulator. 50 insects were used for each dose and 8 doses were used to calculate the $DL_{50}$ or the dose at which 50% of the insects were dead after 24 hours from the treatment. The $DL_{50}$ for the product of Example 1 was 5.9 ng per individual.

Various modifications of the products and method of the invention may be made without departing from the spirit or scope thereof and it is to be understood that the invention is intended to be limited only as defined in the appended claims.

What is claimed is:

1. An ester in all possible isomeric forms and mixtures thereof of the formula

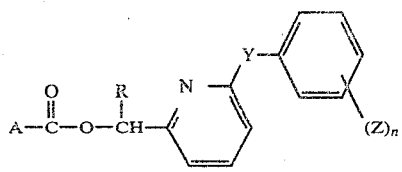

wherein A is

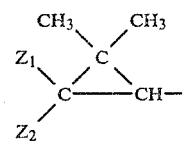

R is selected from the group consisting of hydrogen, —CN and —C≡CH, Y is selected from the group consisting of oxygen and sulfur, Z is selected from the group consisting of alkyl and alkoxy of 1 to 4 carbon atoms, alkylthio and alkylsulfonyl of 1 to 4 carbon atoms, cycloalkyl of 3 to 4 carbon atoms, 3,4-methylenedioxy, chlorine, fluorine and bromine, n is an integer of 0, 1 or 2, $Z_1$ is hydrogen and $Z_2$ is

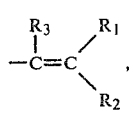

$R_3$ is selected from the group consisting of hydrogen and halogen, $R_1$ and $R_2$ are individually alkyl of 1 to 8 carbon atoms or taken together with the carbon they are attached to form cycloalkyl of 3 to 6 carbon atoms or

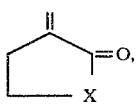

X is selected from the group consisting of oxygen and sulfur.

2. A compound of claim 1 wherein Y is oxygen.

3. A compound of claim 1 or 2 wherein n is 0.

4. A compound of claim 1 or 2 or 3 wherein R is —CN.

5. A compound of claim 1 wherein the cyclopropane moiety has the 1R,cis or 1R, trans configuration.

6. A compound of claim 1 wherein $Z_1$ is hydrogen and $Z_2$ is

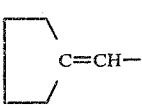

7. A compound of claim 1 wherein $Z_1$ is hydrogen and $Z_2$ is

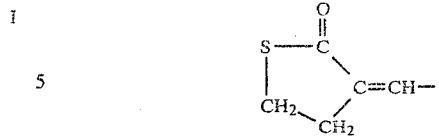

8. A pesticidal composition comprising a pesticidally effective amount of a compound of claim 1 and an inert carrier.

9. A composition of claim 8 wherein Y is oxygen.

10. A composition of claim 8 or 9 wherein n is 0.

11. A composition of claim 8 or 9 or 10 wherein R is —CN.

12. A composition of claim 8 wherein the cyclopropane moiety has the 1R,cis or 1R,trans configuration.

13. A composition of claim 8 wherein $Z_1$ is hydrogen and $Z_2$ is

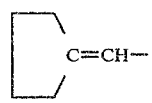

14. A composition of claim 8 wherein $Z_1$ is hydrogen and $Z_2$ is

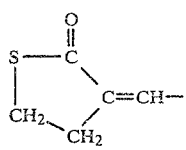

15. A composition of claim 8 wherein the compound is (R,S) α-cyano-(6-phenoxy-2-pyridyl)-methyl (1R,trans) 2,2-dimethyl-3-(cyclopentylidenemethyl)-cyclopropane-carboxylate.

16. An insecticidal composition comprising an insecticidally effective amount of a compound of claim 1 and an inert carrier.

17. A composition for combatting infections caused by acariens in warm-blooded animals, comprising an antiacariendly effective amount of a compound of claim 1 and an inert carrier.

18. An animal feed composition containing an acaricidally effective amount of a compound of claim 1.

19. A method of combatting pests comprising contacting the pests with a pesticidally effective amount of a compound of claim 1.

20. A method of claim 19 wherein Y is oxygen.

21. A method of claim 19 or 20 wherein n is 0.

22. A method of claim 19 or 20 or 21 wherein R is —CN.

23. A method of claim 19 wherein the cyclopropane moiety has the 1R,cis or 1R,trans configuration.

24. A method of claim 19 wherein $Z_1$ is hydrogen and $Z_2$ is

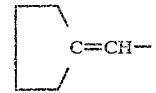

25. A method of claim 19 wherein $Z_1$ is hydrogen and $Z_2$ is

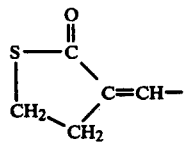

26. The method of claim 19 wherein the compound is (R,S)α-cyano-(6-phenoxy-2-pyridyl)-methyl (1R,trans) 2,2-dimethyl-3-(cyclopentylidenemethyl)-cyclopropane-carboxylate.

27. A method of combatting insects comprising contacting the insects with an insecticidally effective amount of a compound of claim 1.

28. A method of combatting infections contacting acariens with an antiacarienly effective amount of a compound of claim 1.

* * * * *